United States Patent
Parker

(10) Patent No.: US 8,579,809 B2
(45) Date of Patent: Nov. 12, 2013

(54) RADIALLY EXPANDING SURGICAL RETRACTOR

(75) Inventor: Brad Parker, Warsaw, IN (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 1512 days.

(21) Appl. No.: 11/316,176

(22) Filed: Dec. 22, 2005

(65) Prior Publication Data

US 2006/0142643 A1    Jun. 29, 2006

Related U.S. Application Data

(60) Provisional application No. 60/638,902, filed on Dec. 23, 2004.

(51) Int. Cl.
*A61B 1/32*    (2006.01)

(52) U.S. Cl.
USPC ............................................. 600/219

(58) Field of Classification Search
USPC .................... 600/219, 220, 214, 224, 233
See application file for complete search history.

(56) References Cited

U.S. PATENT DOCUMENTS

| | | | |
|---|---|---|---|
| 2,083,573 A * | 6/1937 | Morgan | 600/224 |
| 3,030,947 A | 4/1962 | Engelbert | 128/3 |
| 3,312,222 A | 4/1967 | Dwyer | 128/345 |
| 3,766,910 A | 10/1973 | Lake | 128/20 |
| 3,789,852 A | 2/1974 | Kim et al. | 128/347 |
| 4,130,113 A | 12/1978 | Graham | 128/20 |
| 5,125,396 A | 6/1992 | Ray | 128/20 |
| 5,183,032 A * | 2/1993 | Villalta et al. | 600/224 |
| 5,195,505 A * | 3/1993 | Josefsen | 600/204 |
| 5,505,690 A * | 4/1996 | Patton et al. | 600/210 |
| 5,509,893 A | 4/1996 | Pracas | 600/224 |
| 6,096,046 A | 8/2000 | Weiss | 606/119 |
| 6,354,995 B1 * | 3/2002 | Hoftman et al. | 600/219 |
| 6,709,389 B2 * | 3/2004 | Farascioni | 600/229 |
| 7,060,029 B1 * | 6/2006 | Hajianpour | 600/190 |
| 7,182,730 B2 * | 2/2007 | Fehling | 600/224 |
| 2004/0087833 A1 * | 5/2004 | Bauer et al. | 600/201 |

* cited by examiner

*Primary Examiner* — Rachel Steitz
(74) *Attorney, Agent, or Firm* — Taylor IP, P.C.

(57) ABSTRACT

A radially expanding surgical retractor which includes a base having a thickness, the base having a first slot extending through the thickness in a first arc, and a second slot discrete from the first slot and extending through the thickness in a second arc. The radially expanding surgical retractor further includes a first handle, a second handle, a first blade extending through the first slot and connected to the first handle, and a second blade extending through the second slot and connected to the second handle.

12 Claims, 9 Drawing Sheets

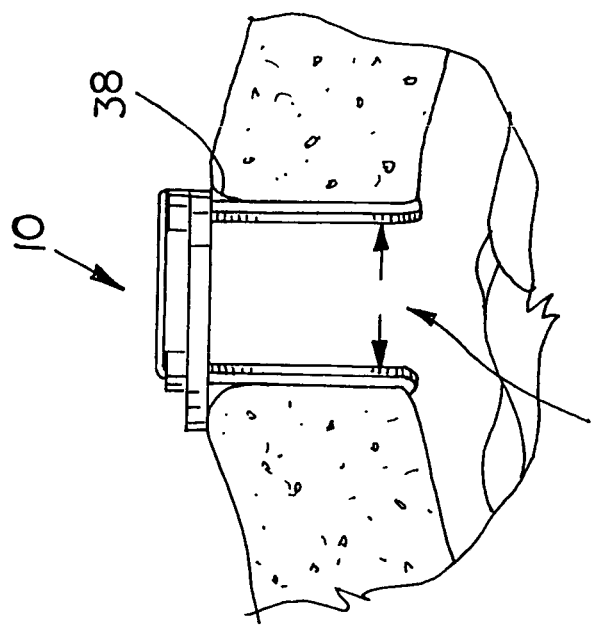
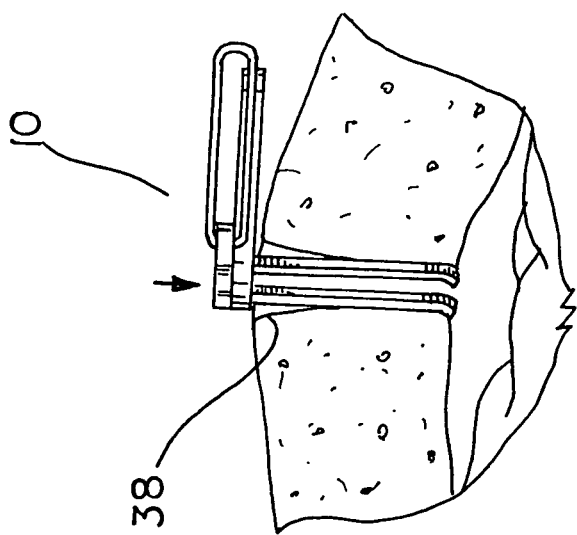
FIG. 7
FIG. 8

RADIALLY EXPANDING SURGICAL RETRACTOR

CROSS REFERENCE TO RELATED APPLICATIONS

This is a non-provisional application based upon U.S. provisional patent application Ser. No. 60/638,902, entitled "RADIAL EXPANDING RETRACTOR", filed Dec. 23, 2004.

BACKGROUND OF THE INVENTION

1. Field of the Invention

The present invention relates to surgical instruments, and, more particularly, to a surgical retractor.

2. Description of the Related Art

Surgical retractors are known which can separate skin tissue, muscle, organs and/or other tissue for the purpose of allowing access to a surgical site. This may typically be done after an incision has been made and the retractor is in inserted into the incision and retracted to expand the incision, for example.

A surgical retractor is known, of the type used to retract tissue or muscles during a surgical operation, which includes an outer ring having a downwardly extending outer blade and an inner ring having a downwardly extending inner blade. The inner ring is nested within the outer ring such that the inner blade is rotatable from a first position overlapped to the outer blade, to a second position in which it is diametrically opposite the outer blade. A first handle is used to hold the outer ring while a second handle rotates the inner ring. The surgical retractor is inserted into an incision with the arcuate blades in the first position and the outer and inner rings are rotated to spread muscle and tissue. A problem with this design is that, with the inner ring nested within the outer ring, it can trap biomatter between the inner ring and outer ring therefore requiring disassembly before cleaning and sterilization. Another problem is that it is a complex design which is relatively costly to manufacture. Another problem with this design is that it requires that the two handles be held to maintain the second position in which the first blade is diametrically opposite the outer blade, thereby not allowing a hands free operation.

A surgical instrument is known for spreading apart the internal organs of a patient. The instrument includes a scissors-like main body portion having a plurality of blades that open to spread apart the area being examined so that a surgical tool can be inserted therein. The surgical tool can pass through a gate formed between the spread-apart blades while maintaining the spread-apart condition of the area being examined. The blades can then be restored to their closed position after the tool is withdrawn. This is a very complex design which is also relatively costly to manufacture and difficult to clean and sterilize.

What is needed in the art is a radially expanding surgical retractor which is cost efficient to manufacture, which is easy to use, clean and sterilize, and which can be used to maintain the spread-apart condition of an incision/surgical site hands-free.

SUMMARY OF THE INVENTION

The present invention provides a radially expanding surgical retractor with expanding blades which are slidable/rotatable in slots in a base, and which blades are actuated by handles which can be locked in a blades expanded position.

The invention comprises, in one form thereof, a radially expanding surgical retractor which includes a base having a thickness, the base having a first slot extending through the thickness in a first arc, and a second slot discrete from the first slot and extending through the thickness in a second arc. The radially expanding surgical retractor further includes a first handle, a second handle, a first blade extending through the first slot and connected to the first handle, and a second blade extending through the second slot and connected to the second handle.

The invention comprises, in another form thereof, a method of using a radially expanding surgical retractor, including the steps of: providing a base having a thickness, the base including a first slot extending through the thickness in a first arc, the base including a second slot discrete from the first slot and extending through the thickness in a second arc, a first handle, a second handle, a first blade extending through the first slot and connected to the first handle, a second blade extending through the second slot and connected to the second handle and a bale rotatably mounted to one of the first handle and the second handle; inserting the first blade and the second blade into a surgical incision; rotating at least one of the first handle and the second handle into a near vicinity of an other of the first handle and the second handle, thereby positioning the first blade and the second blade in an opposed relationship and retracting the incision; and locking the first blade and the second blade in the opposed relationship by pivoting the bale so that the bale is inserted into a catch on an other of the first handle and the second handle.

An advantage of the present invention is that it can retract a surgical incision.

Another advantage of the present invention is that it can be used to maintain the spread-apart condition of an incision/surgical site hands-free.

Yet another advantage of the present invention is that it is cost efficient to manufacture.

Yet another advantage of the present invention is that it is easy to use.

Yet another advantage of the present invention is that it is easy to clean.

Yet another advantage of the present invention is that it is easy to sterilize.

Yet another advantage of the present invention is that it is a reliable design.

Yet another advantage of the present invention is that it is an ergonomic design.

Yet another advantage of the present invention is that it is easily scalable in size to fit a variety of surgical incisions and/or is adaptable for a variety of surgical situations.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 7 is cross-sectional view taken along section line 7-7 in FIG. 3;

FIG. 8 is cross-sectional view taken along section line 8-8 in FIG. 6;

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
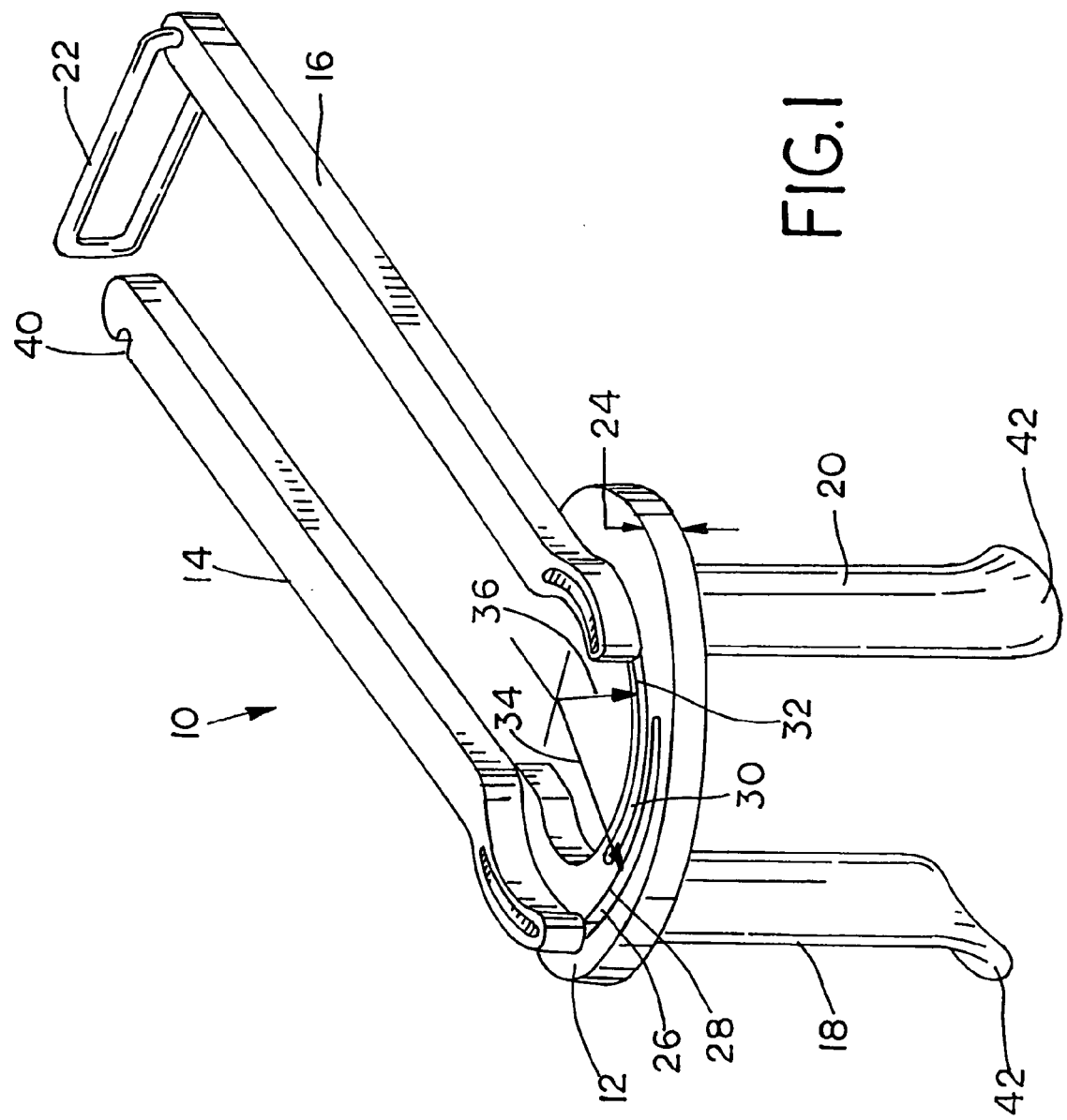
FIG. 1 is a perspective view of an embodiment of a radially expanding surgical retractor according to the present invention.

Referring now to the drawings, and more particularly to FIG. 1, there is shown radially expanding surgical retractor 10 which generally includes a base 12, a first handle 14, a second handle 16, a first blade 18, a second blade 20 and a bale 22.

Figure 3:
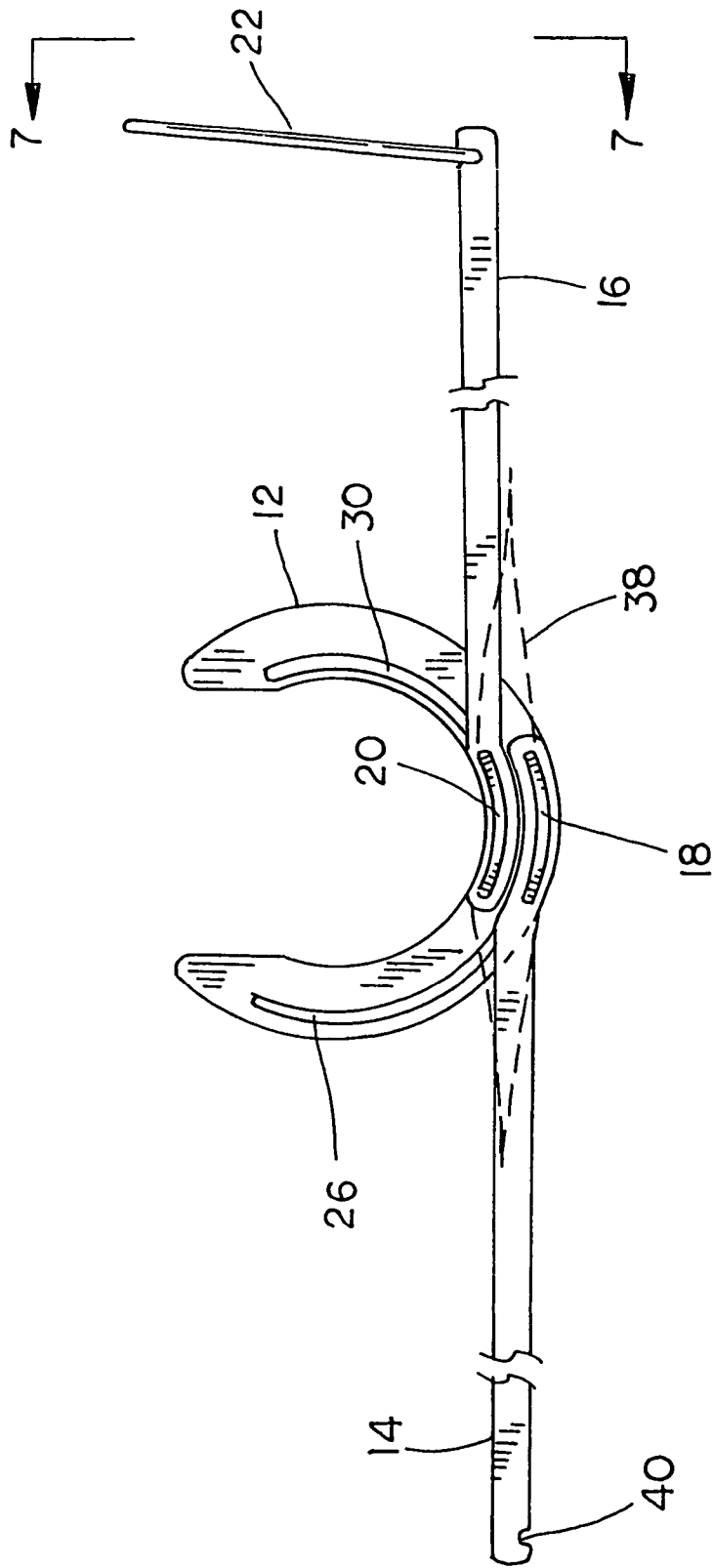
FIG. 3 is a fragmentary top view of the radially expanding surgical retractor of FIG. 1 shown inserted into a surgical incision.
Figure 4:
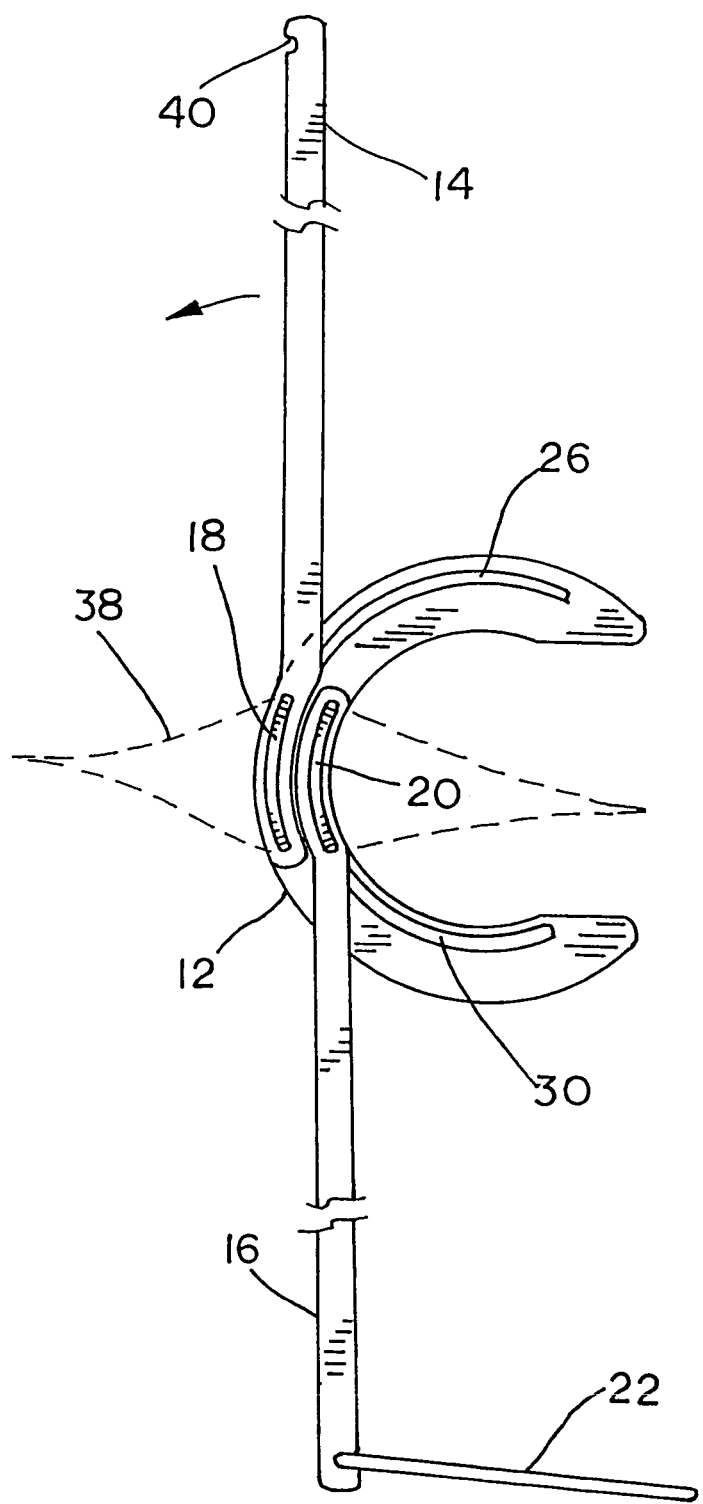
FIG. 4 is a fragmentary top view of the radially expanding surgical retractor of FIG. 3 shown after the entire assembly is rotated in the surgical incision.
Figure 5:
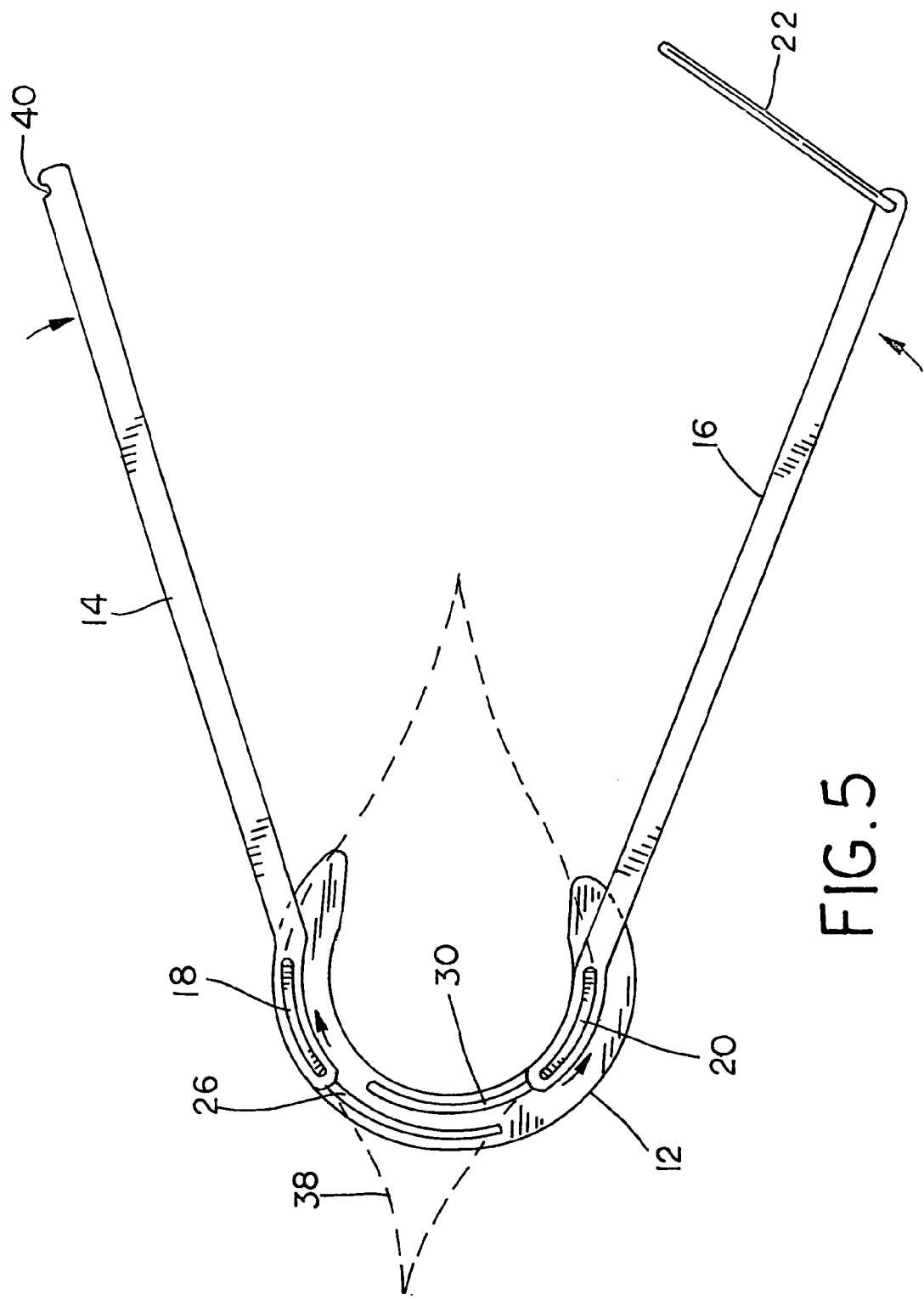
FIG. 5 is a top view of the radially expanding surgical retractor of FIG. 4 shown as the retractor blades are being radially expanded into the surgical incision.

Base 12 includes a thickness 24, and a first slot 26 which extends through thickness 24 in a first arc 28. A second slot 30 is discrete from first slot 26 and extends through thickness 24 in a second arc 32. First arc 28 has a first radius 34, and second arc 32 has a second radius 36, and second radius 36 can be less than first radius 34 to be able to nest first blade 18 and second blade 20 when first inserting retractor 10 into an incision/surgical site 38 (FIG. 3).

Figure 2:
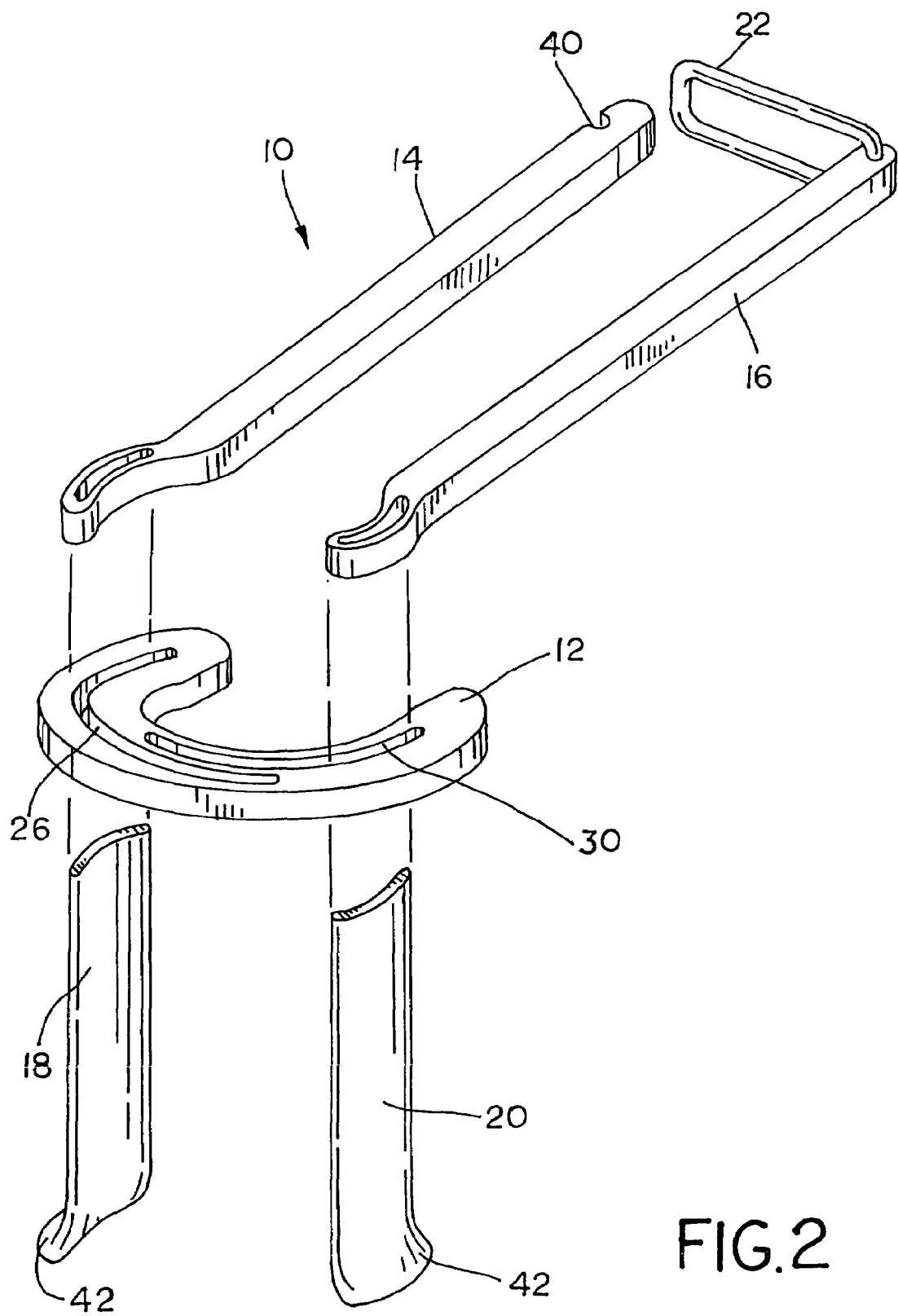
FIG. 2 is a perspective exploded view of the radially expanding surgical retractor of FIG. 1.

As shown particularly in FIG. 2, first blade 18 extends through first slot 26 and connects to first handle 14. Second blade 20 extends through second slot 30 and connects to second handle 16. First blade 18 is slidable within first slot 26 and/or second blade 20 is slidable within second slot 30. Although both first blade 18 and second blade 20 are shown slidable within their respective slots 26, 20, either first blade 18 and second blade 20 can be fixed relative to base 12, for example.

Bale 22 is rotatably connected to first handle 14 or second handle 16. The other of first handle 14 or second handle 16 includes a catch 40 for bale 22. Catch 40 can be an indent in the handle, for example.

Figure 6:
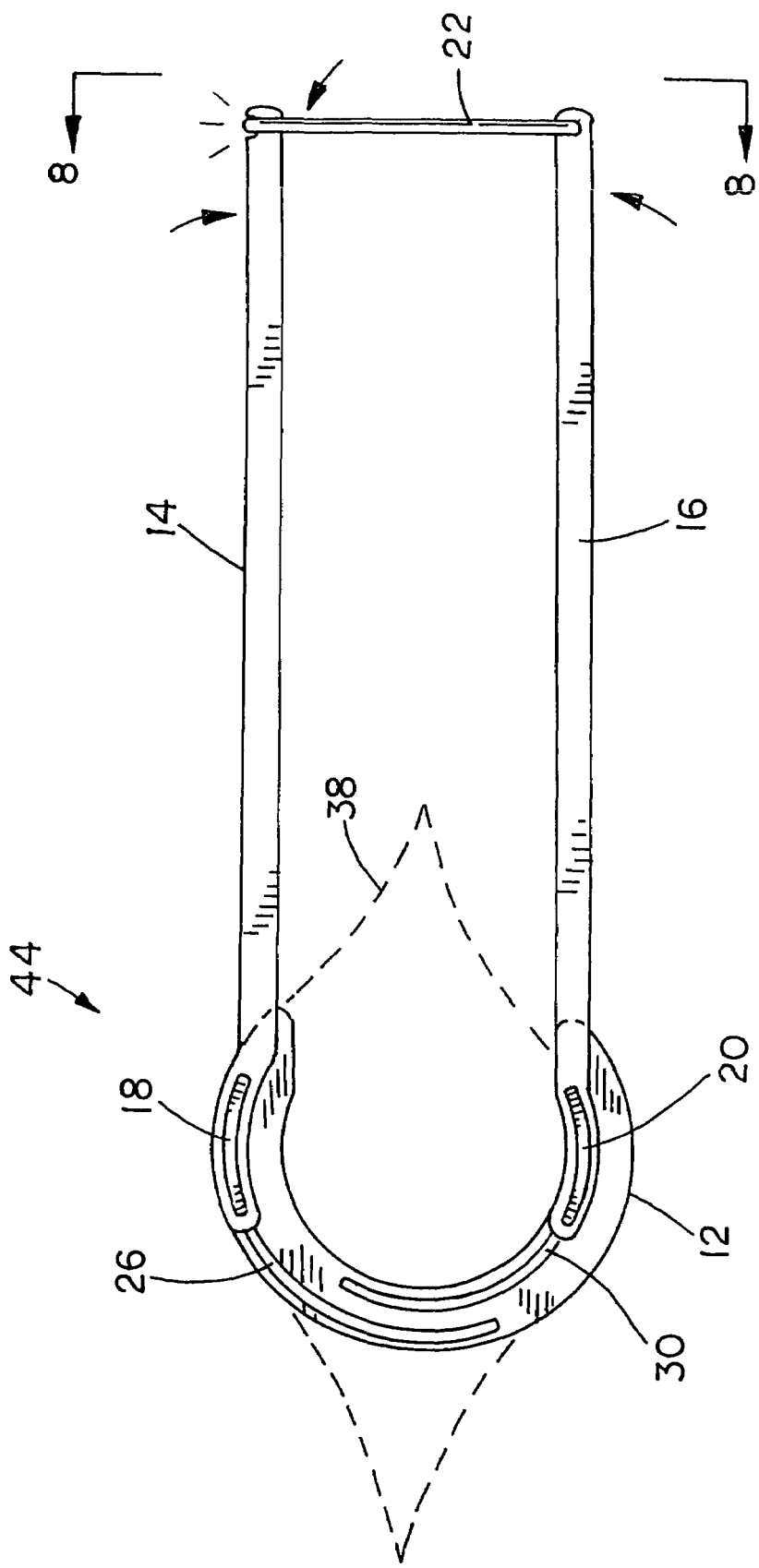
FIG. 6 is a top view of the radially expanding surgical retractor of FIG. 5 shown as the retractor blades are fully radially expanded into the surgical incision, and the handles are locked by a bale.

First blade 18 and/or second blade 20 can have a flange 42 extending outwardly from base 12. As shown particularly in FIGS. 3-8 first blade 18 and/or second blade 20 are rotatable to an open position 44 (FIGS. 6 and 8) where first blade 18 is opposed to second blade 20, and bale 22 is captive at second handle 16 and can connect to catch 40 at first handle 14 when radially expanding surgical retractor 10 is in open position 44. Alternatively, bale 22 is captive at first handle 14 and can connect to a catch on second handle 16. Although first blade 18 and second blade 20 are shown opposed at approximately 180° in FIG. 6, they can be opposed at other angles varying from 0° to 360°, and can be opposed at 120° or 240°, for example.

Figure 9:
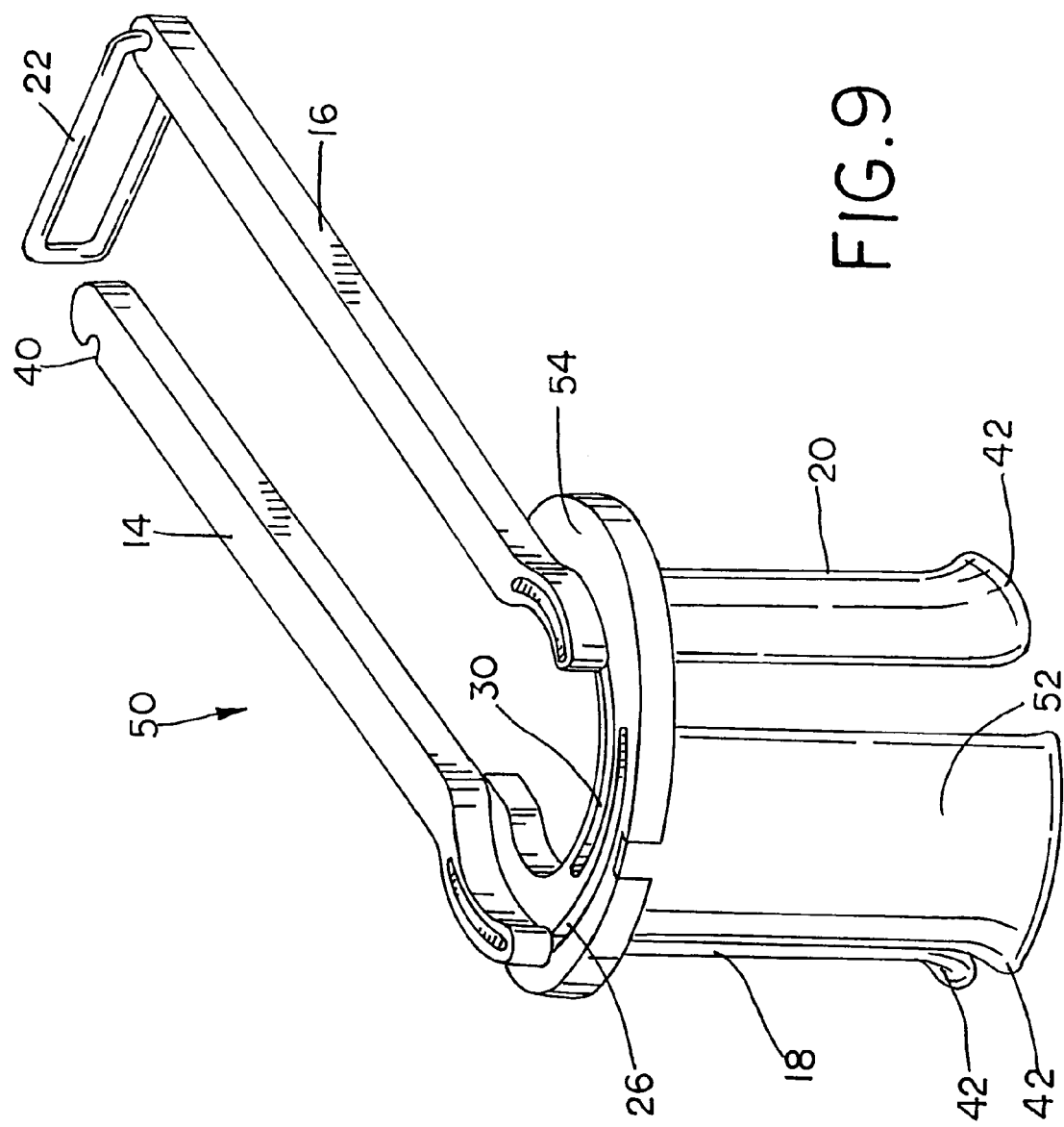
FIG. 9 is a perspective view of another embodiment of a radially expanding surgical retractor according to the present invention.

Radially expanding surgical retractor 50 of FIG. 9 is similar to radially expanding surgical retractor 10 of FIG. 1; however, retractor 50 includes a third blade 52 fixedly connected to base 54. When handles 14, 16 are diametrically opposed similar to FIG. 3, blades 18, 20 and 52 are nested together. Blades 18, 20 and 52 can be opposed at 90° separations, 120° separations, other angles varying from 0° to 360°, or can be opposed at varying angles between the blades.

Figure 10:
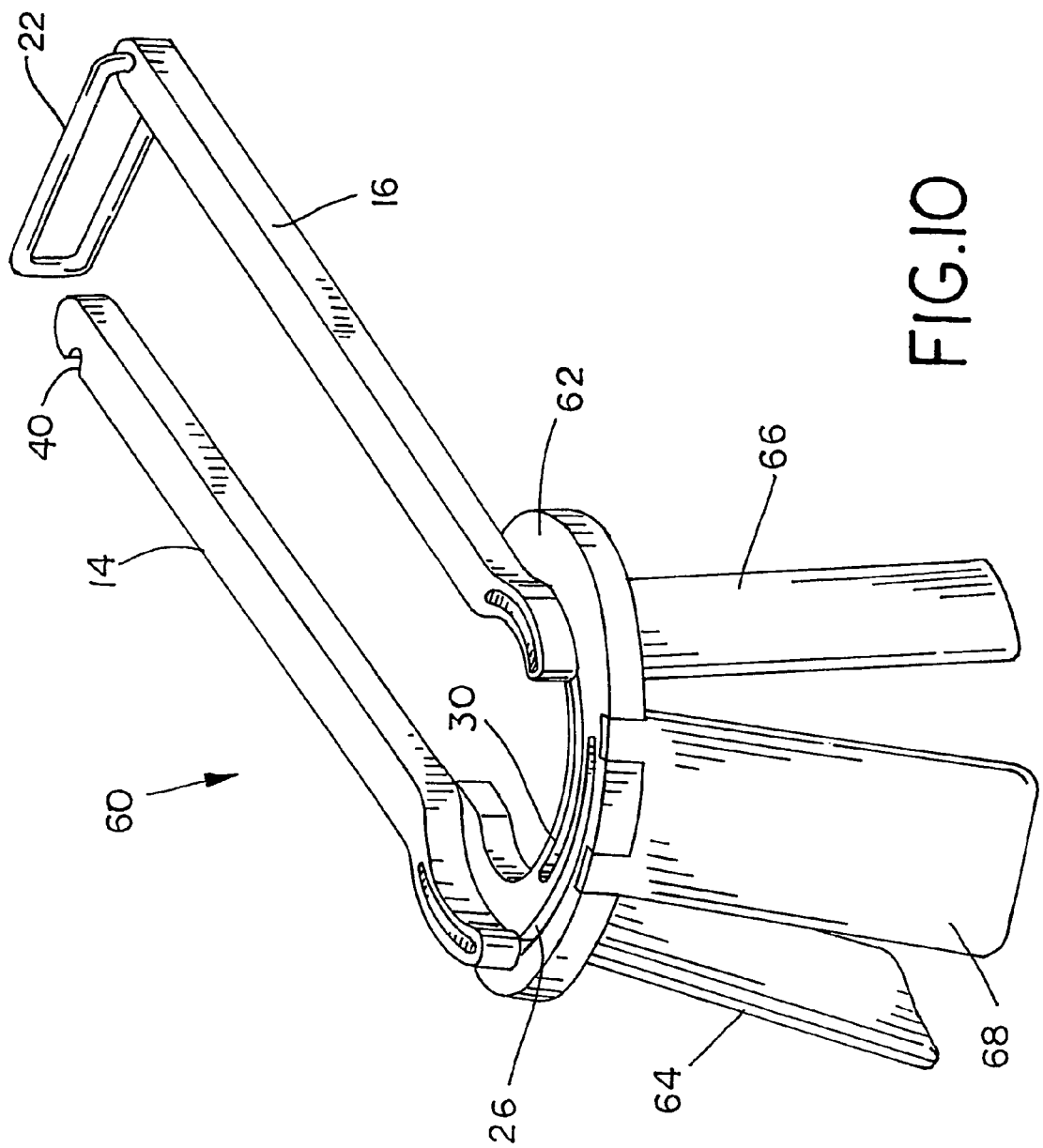
FIG. 10 is a perspective view of another embodiment of a radially expanding surgical retractor according to the present invention.

Radially expanding surgical retractor 60 of FIG. 10 include base 62, first blade 64, second blade 66 and third blade 68, and is otherwise similar to retractors 10 and 50. Importantly, at least one of blades 64, 66 and 68 extends outwardly relative to base 62, which can be instead of, or in addition to, an outwardly extending flange as previously discussed. Blade 68 is fixedly attached to base 62, whereas blades 64 and 66 are moveable within their respective slots. The outward extensions of the blades or flanges can improve access to a surgical site and/or expansion thereof without the need for a larger incision, thereby making the present invention compatible with minimally invasive surgical procedures.

As can be seen in FIGS. 1-6, 9, and 10, both first arc 28 and second arc 32 have two sides with curved surfaces that face each other. Blades 18 and 20 likewise have curved surfaces that correspond to the curved surfaces of the respective arcs. The blades are configured to move in a curved direction defined by the curvature of the arcs as can be seen in the figures.

The size and shape of the handles and blades can vary, and importantly, the size (radial extent) of the base can change depending on the surgical procedure. For example, larger bases, which allow a larger radial expansion of the blades, may be suitable for minimally invasive, or other, hip surgery, whereas smaller bases may be more suitable for spinal surgery.

In use, the present invention discloses a method of using a radially expanding surgical retractor 10, including the steps of: providing a base 12 having a thickness 24, base 12 having a first slot 26 extending through thickness 24 in first arc 28, base 12 including a second slot 30 discrete from first slot 26 and extending through thickness 24 in second arc 32, first handle 14, second handle 16, first blade 18 extending through first slot 26 and connected to first handle 14, second blade 20 extending through second slot 30 and connected to second handle 16, and a bale 22 rotatably mounted to one of first handle 14 and second handle 16; inserting first blade 18 and second blade 20 into surgical incision 38; rotating first handle 14 and/or second handle 16 into a near vicinity of an other of first handle 14 and second handle 16, thereby positioning first blade 18 and second blade 20 in an opposed relationship 44 and retracting incision 38; and locking first blade 18 and second blade 20 in the opposed relationship 44 by pivoting bale 22 so that bale 22 is inserted into catch 40. The method according to the present invention works equally well for any of the embodiments of the present invention.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A radially expanding surgical retractor, comprising:
a base having a thickness, said base including a first slot extending through said thickness in a first arc, and a second slot discrete from said first slot and extending through said thickness in a second arc, said first slot having two sides with curved facing surfaces defined by said first arc;
a first handle;
a second handle;
a first blade extending through said first slot and connected to said first handle; and
a second blade extending through said second slot and connected to said second handle.

2. The radially expanding surgical retractor of claim 1, further including a third blade fixedly connected to said base.

3. The radially expanding surgical retractor of claim 1, wherein said first arc has a first radius, said second arc has a second radius, said second radius less than said first radius.

4. The radially expanding surgical retractor of claim 3, wherein at least one of said first blade is slidable within said first slot and said second blade is slidable within said second slot.

5. The radially expanding surgical retractor of claim 1, further including a bale rotatably connected to one of said first handle and said second handle.

6. The radially expanding surgical retractor of claim 5, wherein an other of said first handle and said second handle includes a catch for said bale.

7. The radially expanding surgical retractor of claim 1, wherein at least one of said first blade and said second blade has a flange extending outwardly relative to said base.

8. The radially expanding surgical retractor of claim 1, wherein at least one of said first blade and said second blade extends outwardly relative to said base.

9. A radially expanding surgical retractor, comprising:
a base having a thickness, said base including a first slot extending through said thickness in a first arc, and a second slot discrete from said first slot and extending through said thickness in a second arc;
a first handle;
a second handle;
a first blade extending through said first slot and connected to said first handle; and
a second blade extending through said second slot and connected to said second handle; and
a bale rotatably connected to one of said first handle and said second handle, an other of said first handle and said second handle includes a catch for said bale, said catch is an indent in said other of said first handle and said second handle.

10. A radially expanding surgical retractor, comprising:
a base having a thickness, said base including a first slot extending through said thickness in a first arc, and a second slot discrete from said first slot and extending through said thickness in a second arc;
a first handle;
a second handle;
a first blade extending through said first slot and connected to said first handle;
a second blade extending through said second slot and connected to said second handle, at least one of said first blade and said second blade are rotatable to an open position where said first blade is opposed to said second blade, further including a bale captive at one of said first handle and said second handle which connects to a catch at an other of said first handle and said second handle when said radially expanding surgical retractor is in said open position.

11. A method of using a radially expanding surgical retractor, comprising the steps of:
providing a base having a thickness, said base including a first slot extending through said thickness in a first arc, said base including a second slot discrete from said first slot and extending through said thickness in a second arc, a first handle, a second handle, a first blade extending through said first slot and connected to said first handle, a second blade extending through said second slot and connected to said second handle and a bale rotatably mounted to one of said first handle and said second handle;
inserting said first blade and said second blade into a surgical incision;
rotating at least one of said first handle and said second handle into a near vicinity of an other of said first handle and said second handle, thereby positioning said first blade and said second blade in an opposed relationship and retracting said incision; and
locking said first blade and said second blade in said opposed relationship by pivoting said bale so that said bale is inserted into a catch on an other of said first handle and said second handle.

12. A radially expanding surgical retractor, comprising:
a base having a thickness, said base including a first slot extending through said thickness in a first arc, and a second slot discrete from said first slot and extending through said thickness in a second arc, said first slot having two sides defined by said first arc;
a first handle;
a second handle;
a first blade extending through said first slot and connected to said first handle; and
a second blade extending through said second slot and connected to said second handle, said first arc having a first radius, said second arc having a second radius, said second radius being less than said first radius, said first blade having an arced surface that corresponds to said first arc, said first blade being configured to move in a curved direction defined by said first arc.

* * * * *